US00PP12331P2

(12) United States Plant Patent
Friday

(10) Patent No.: US PP12,331 P2
(45) Date of Patent: Jan. 1, 2002

(54) PEACH TREE NAMED 'P.F. 20-007'

(76) Inventor: Paul Jan Friday, P.O. Box 850, Coloma, MI (US) 49038

( * ) Notice: Subject to any disclaimer, the term of this patent is extended or adjusted under 35 U.S.C. 154(b) by 0 days.

(21) Appl. No.: 09/177,293

(22) Filed: Oct. 22, 1998

(51) Int. Cl.[7] ..... A01H 5/00
(52) U.S. Cl. ..... Plt./198
(58) Field of Search ..... Plt./198

(56) References Cited

U.S. PATENT DOCUMENTS

PP1,925 P * 3/1960 Tremmel et al. ..... Plt./198
PP9,895 P * 5/1997 Friday ..... Plt./198

* cited by examiner

*Primary Examiner*—Howard J. Locker
*Assistant Examiner*—Wendy A. Baker

(57) ABSTRACT

A new and distinct variety of peach *Prunus persica,* tree having the following unique combination of desirable features:

1. The new and distinct variety of peach is of spreading growth and a regular and productive bearer of large peaches having a diameter of between 2½" and 3" while bearing heavy crops exceeding 600 bushels per acre in a test block in Michigan. The tree planting was based on 300 trees per acre.
2. Producing a very firm fruit having a resilient flesh texture.
3. Blossoms are non-showy when in full bloom.
4. A substantially spherical to oblate fruit with skin of red overlaying a medium yellow color at maturity.
5. Mid-season maturing fruit of good taste.
6. A mid-season maturing fruit of good storage and shelf life.

2 Drawing Sheets

ORIGIN OF VARIETY

The new peach tree (*Prunus persica*) (hereinafter referred to as the P.F. 20-007 peach tree) was originated by Paul Friday in the experimental orchard, which is maintained for the purpose of breeding peach trees, at Paul Friday Farms Inc., located in Coloma, Mich. Coloma is located in the southwest section of Michigan.

In an ongoing mass selection breeding program, superior seedlings of unrecorded parentage are maintained as seed sources for the production of seeds which are collected and planted in mass. The seed producing parent trees are maintained solely as proprietary trees for breeding purposes and have not been released from the experimental orchard, where such trees can be evaluated for their adaptability to local and regional growing conditions. Seeds resulting from open pollination of the trees in the experimental orchard are regularly planted in mass to produce new populations of seedlings which are cultured and monitored to maturity. Trees with superior attributes are retained for further observation and testing, and contribute seeds to advancing generations of new populations of seedlings.

The tree of this application, P.F. 20-007, was a selection from one such cultivated seedling population, and was based on the numerous superior genetic attributes of this tree which are described in the botanical descriptions to follow. While not exhaustive, the botanical descriptions to follow are believed to represent a reasonably complete botanical description of the new peach tree which is sufficiently detailed to distinguish the tree from the most closely related trees within the same market class.

ASEXUAL REPRODUCTION OF THE VARIETY

The new and distinct variety of peach tree was asexually propagated by budding onto 'Bailey' rootstock as performed in the experimental orchard of Paul Friday Farms Inc., located in Coloma, Mich. The so stated propagation demonstrates that such reproduction of the characteristics of the tree are consistent and are established and transmitted through succeeding propagation.

SUMMARY OF THE VARIETY

The new and distinct variety of peach tree is of moderate spreading growth. A distinct characteristic of the P.F. 20-007 peach tree is that it has large, strong right angle branching to support its heavy crops of large fruit. While fruit set is medium, this variety yields very big crops due to large fruit size, providing extraordinary yields and is a regular and productive bearer of large peaches.

The blossoms of the present peach tree bloom in mid-season and are characterized as being non-showy and do not open much past a vertical state only, opening to a diameter of about ½ inch diameter during full bloom with its pistil protruding beyond the plane of the opened blossom petals.

The fruit at maturity has crisp flesh of very clear yellow with red around the pit.

The skin is smooth, having little down, and is sixty to eighty percent red or more overlying medium-yellow color. At maturity, the peach is spherical, having an average diameter ranging between 2½ inches to 3 inches.

The fruit has a firm flesh and may be described as resilient to the extent that the flesh is yieldable and restorable to its original state when subjected to impact forces which may cause permanent deformities in peaches of commercial varieties. The firmness of fruit facilitates handling and packaging of the peaches without damaging the same for shipment. This results in less spoilage and also increases the shelf life.

The fruit matures in the mid-part of the peach growing season in southwestern Michigan.

BRIEF DESCRIPTION OF THE PHOTOGRAPHS

In the accompanying photographic illustrations, the first photograph was taken at a maturity stage of firm ripeness and demonstrates a typical fruit positioned to show the blossom end exhibiting the round to slightly oblate fruit shape and the exceptional symmetry of the fruit. The color of the extensive solid blush and slightly mottled over-color patterns are depicted over the ground color of the fruit skin. Shown also is a fruit that has been split on a plane ninety degrees to the suture plane to depict the fruit flesh in cross-section. The conformance of the pit cavity is illustrated, as well as the desirable ratio of the size of the stone to the fruit size of this tree. The clear flesh texture, yellow color, and red around the pit are also demonstrated.

The second photograph depicts the stem end of the fruit showing its short stem cavity and the limb imprints, demonstrating how tightly the fruit grows to the tree. Predominant smooth red color over yellow is also shown.

The third photograph demonstrates stems of current season's growth at a stage of about harvest season. It also shows young stem coloration, the top side of leaves, the shape, color and character of leaves, and the internode length.

DESCRIPTION OF VARIETY

The detailed botanical description of the foliage and fruit of the new variety of peach tree is based upon observations of the specimens grown at Coloma, Mich. with the color terminology, other than the terminology expressed in common terms, in accordance with the Pantone Matching System (PMS) as used internationally to identify printed colors.

Tree:

*Height.*—Unpruned 16'.

*Width.*—Unpruned 18'.

*Size.*—Medium-large.

*Vigor.*—Medium vigor, 2' to 3' per year.

*Density.*—Medium, pruning requirements heavy.

*Form.*—With routine pruning, this variety makes a large, spacious vase-shaped tree with strong right-angle branching.

*Production.*—This variety is productive, growing very heavy crops of large fruit even if thinned only to close spacings, keeping the fruit from touching. Second generation trees withstood winter temperatures in 1994 of 18 degrees Fahrenheit below zero without causing much damage to the trees.

*Bearer.*—Consistent.

*Disease resistance to bacterial leaf and fruit spot.*—Very good. No unusual susceptibility to diseases common to peach has been noted.

Trunk:

*Size.*—Stocky, large for Michigan conditions. Six-year old tree has 6" diameter trunk at 2' from ground.

*Surface.*—Smooth to medium shaggy.

*Color.*—Medium brown.

Branches:

*Size.*—Large.

*Surface.*—Smooth to medium.

*Internode length.*—Standard size, normal at start of Season and small at the end.

*Lenticels.*—Medium number, the size is ½" to 1" in length.

*Color.*—Dark gray.

Leaves:

*Size.*—Medium. Average length — 6". Average width — 1¼".

*Form.*—Lanceolate — pointed. Apex acute to acuminate. Base attenuate to acute.

*Thickness.*—Medium.

*Texture.*—Medium.

*Margin.*—Very finely serrated.

*Petiole.*—Medium length — medium thickness.

*Gland.*—Small, oval, usually one located on each side of the leaf base.

*Color.*—Upper surface green (5747u). Lower surface dull green (581u).

Flower buds:

*Size.*—Medium.

*Length.*—Medium.

*Shape.*—Typical of peach.

Flowers:

*Blooming period.*—Normally May 1 to May 6. Each bloom lasts about 10 days.

*Size.*—Small, non-showy, about ½" diameter.

*Number.*—About 4 per node.

*Pollen.*—Present, self-fertilizing.

*Color.*—Pink.

*Fragrance.*—None.

Fruit:

*Maturity when described.*—Firm ripe.

*Average date of first picking.*—In Michigan, August 25. Fruit matures very evenly and can be harvested in two or three pickings.

*Average date of last picking.*—In Michigan, September 1.

*Productivity.*—Over 600 bushels per acre.

*Size.*—Notably large, 95% of the fruit is 2½" or larger in diameter and over one-half is 2¾" or larger, and a substantial amount of fruit is 3" in diameter or larger.

*Form.*—Round to oblate, its diameter is somewhat greater than its height.

*Suture.*—Medium.

Skin:

*Thickness.*—Medium.

*Texture.*—Medium.

*Tendency to crack.*—None.

*Down.*—Slight.

*Color.*—60% to 80% red (1665u). Background color yellow (106c).

Flesh:

*Texture.*—Firm, clear without fiber.

*Ripens.*—Evenly.

*Flavor.*—Excellent — a balance between sweet and acid.

*Aroma.*—Pleasant.

*Color.*—Yellow (129c), pit cavity red (1665u).

Stone:

*Type.*—Freestone.

*Size.*—Average length 1½"; average width 1⅛"; average thickness ¾".

*Form.*—Ovid.

*Base.*—Straight.

*Apex.*—Pointed.

*Sides.*—Nearly equal.

*Surface.*—Furrowed.

*Color.*—Reddish brown (1797u).

*Tendency to crack.*—Slight, about 3%.

Use: Dessert.

Shipping quality: Excellent.

Keeping quality: Good. Can be kept for up to 3 weeks in deep refrigeration.

The tree and its fruits herein described may vary in slight detail as a result of differences in climatic or soil conditions or cultural practices under which the tree may be grown. It is to be understood that the description of the new variety as set forth herein is that of the tree grown under the ecological conditions prevailing at Coloma, Mich.

What is claimed is:

1. A new and distinct variety of peach tree substantially as illustrated and described.

* * * * *

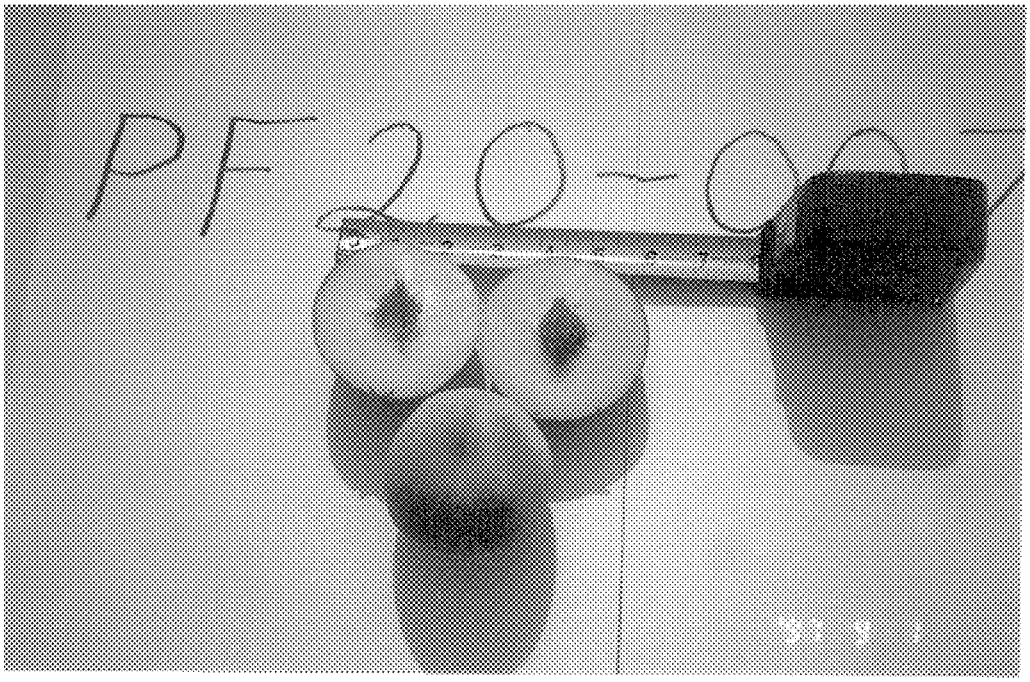
PF20-067
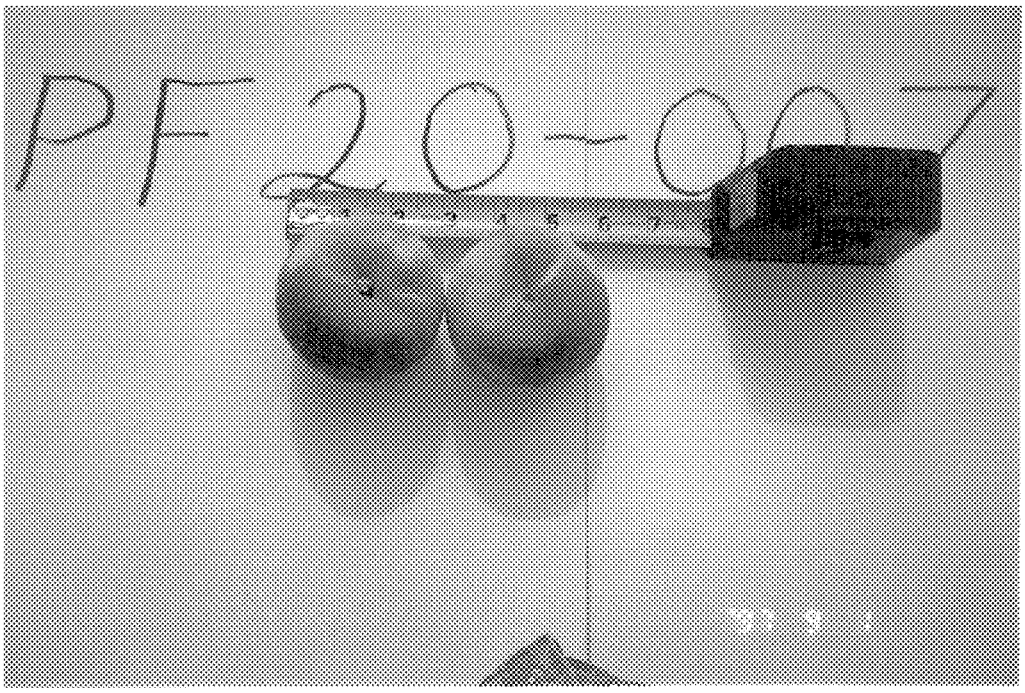
PF20-067

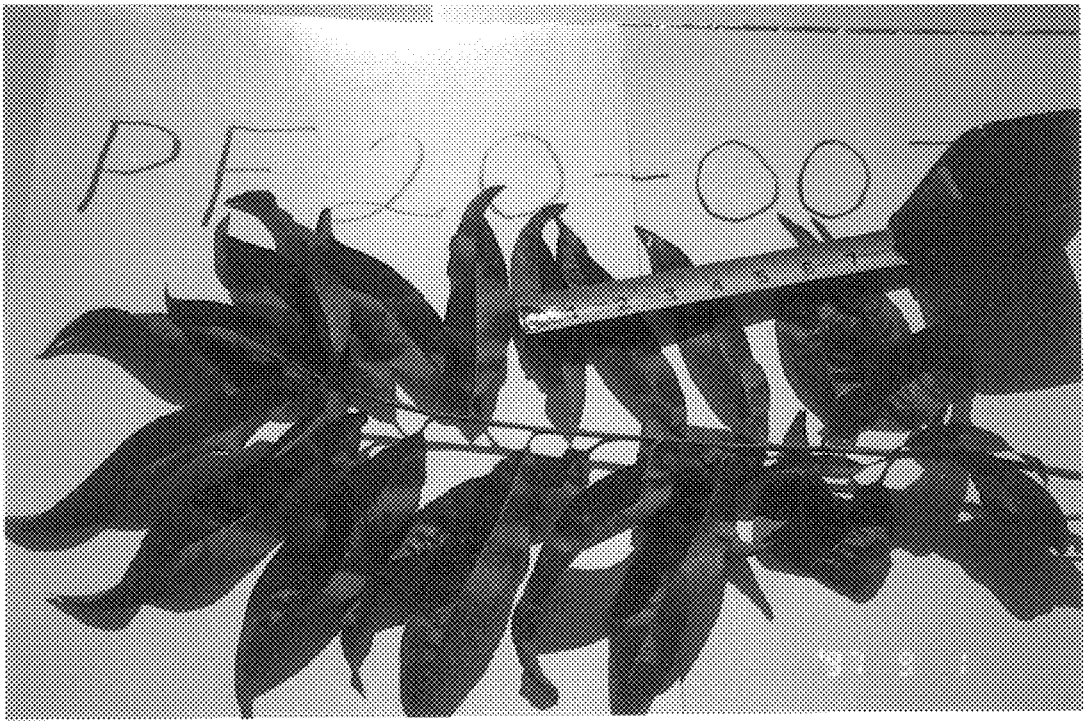
PP12,331-00